(12) United States Patent
Calisse

(10) Patent No.: US 7,611,531 B2
(45) Date of Patent: Nov. 3, 2009

(54) STENT

(75) Inventor: Jorge Calisse, Berlin (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 66 days.

(21) Appl. No.: 11/435,260

(22) Filed: May 16, 2006

(65) Prior Publication Data

US 2006/0206195 A1  Sep. 14, 2006

Related U.S. Application Data

(63) Continuation of application No. 10/241,523, filed on Sep. 12, 2002, now abandoned.

(30) Foreign Application Priority Data

Sep. 18, 2001  (EP)  .................................. 01122285

(51) Int. Cl.
*A61F 2/06* (2006.01)
(52) U.S. Cl. ..................................... 623/1.15
(58) Field of Classification Search ................ 623/1.15, 623/1.18, 1.2; 606/191, 194, 195, 198
See application file for complete search history.

(56) References Cited

U.S. PATENT DOCUMENTS

| 5,733,303 | A |   | 3/1998  | Israel et al. |
| 5,776,181 | A | * | 7/1998  | Lee et al. ..................... 623/1.15 |
| 5,810,872 | A |   | 9/1998  | Kanesaka et al. |
| 5,827,321 | A |   | 10/1998 | Roubin et al. |
| 5,853,419 | A |   | 12/1998 | Imran |
| 5,922,021 | A | * | 7/1999  | Jang ........................... 623/1.15 |
| 6,017,365 | A |   | 1/2000  | Von Oepen |
| 6,048,361 | A |   | 4/2000  | Von Oepen |
| 6,068,656 | A |   | 5/2000  | Von Oepen |
| 6,068,658 | A |   | 5/2000  | Insall et al. |
| 6,193,747 | B1 |  | 2/2001  | von Oepen |
| 6,261,318 | B1 |  | 7/2001  | Lee et al. |
| 2003/0055487 | A1 | | 3/2003 | Calisse |

FOREIGN PATENT DOCUMENTS

| WO | WO 99/17680 A1 | 4/1999 |
| WO | WO 99/38456 A1 | 8/1999 |
| WO | WO 9938458    | 8/1999 |
| WO | WO 99/49928 A1 | 10/1999 |

OTHER PUBLICATIONS

U.S. Appl. No. 10/241,523, Mail Date Aug. 18, 2004, Office Action.

(Continued)

*Primary Examiner*—Kevin T Truong
(74) *Attorney, Agent, or Firm*—Workman Nydegger

(57) ABSTRACT

A stent has a tubular flexible body with a wall formed of a web structure. The web structure has a plurality of neighboring web patterns which include webs arranged side by side. The web patterns are interconnected via at least one connection element. To prevent the connection element from moving out of the plane of the wall during expansion, the connection elements are each provided with connection webs arranged at an angle relative to one another and interconnected via hinges.

14 Claims, 4 Drawing Sheets

OTHER PUBLICATIONS

U.S. Appl. No. 10/241,523, Mail Date Oct. 25, 2004, Office Action.
U.S. Appl. No. 10/241,523, Mail Date Mar. 8, 2005, Office Action.
U.S. Appl. No. 10/241,523, Mail Date Jun. 3, 2005, Office Action.
U.S. Appl. No. 10/241,523, Mail Date Aug. 23, 2005, Office Action.
U.S. Appl. No. 10/241,523, Mail Date Nov. 16, 2005, Office Action.
U.S. Appl. No. 10/241,523, Mail Date Apr. 27, 2006, Office Action.

* cited by examiner

STENT

BACKGROUND OF THE INVENTION

1. Field of the Invention

The present invention generally relates to stents that are implanted into a body vessel. More specifically, the present invention relates to an expandable stent having a tubular flexible body with a wall formed of a web structure.

2. Background Information

Very different types of stents are already known from the prior art. For example, there are coronary stents such as balloon expanded stents or self-expandable stents. The stent forms a vascular prosthesis made from a physically compatible material. The stent or stent prosthesis is used for expanding blood vessels, or also other body orifices, and for keeping the vessels or orifices in an expanded state. To this end, the stent is normally positioned in a non-expanded state in a patient's body, usually with the help of a balloon catheter onto which the stent is crimped, and is then expanded. During expansion the individual stent portions of the stent are deformed, so that the stent remains in its expanded form in a permanent way.

A stent of the type indicated is disclosed in German Utility Model Patent Publication DE-U-297 08 689.8. In this stent, several S-shaped connection elements are provided as connectors between the web patterns of the web structure of the stent wall. Although these connection elements in the non-expanded state result in a very flexible stent construction and, in the expanded state, in a stent construction with a high radial force or radial-force absorbing capacity, improvements are nevertheless possible as it cannot be ruled out all the time that during expansion the connection elements bulge outwards or inwards from the wall plane, whereby the surrounding tissue is slightly injured and the formation of thromboses or restenoses is promoted.

In view of the above, it will be apparent to those skilled in the art from this disclosure that there exists a need for an improved stent. This invention addresses this need in the art as well as other needs, which will become apparent to those skilled in the art from this disclosure.

SUMMARY OF THE INVENTION

It is therefore the object of the present invention to provide a stent, which in the non-expanded state is very flexible and in the case of which it can be prevented during expansion that the connection elements can move out of the wall surface of the stent.

This object is achieved by the features of a stent comprising a tubular flexible body with a wall having a web structure that can be transformed from a non-expanded state into an expanded state. The web structure comprises a plurality of neighboring web patterns which include webs arranged side by side, and adjacent pairs of the web patterns being interconnected by at least one connection element. Each of the connection elements comprises three connection webs arranged at an angle relative to one another and interconnected via a pair of hinges.

The stent according to the invention yields a very flexible structure during bending and compression. It is possible in a particularly advantageous manner to prevent a situation where upon expansion of the stent the connection elements impair the tissue in the expanded state of the stent, and where the lumen of the stent interior is reduced.

The reason for such an advantageous effect must above all be seen in the fact that the connection elements become shorter both during bending (e.g., when the stent is placed in a curved vessel) and during expansion (e.g., during expansion by means of the balloon), which is achieved by the special arrangement of the connection webs of the connection elements with the hinges or joints provided for.

The connection webs of the connection elements in the non-expanded or compressed state of the web structure are arranged relative to one another at least approximately, preferably exactly, at a right angle.

It is thus possible to make the width of each of the connection webs equal or, in order to achieve an enhanced flexibility, to make the width of the central connection web slightly smaller than the width of the connection webs joining the central web.

The connection webs which are connected to the neighboring webs of the web structure are mounted in a particularly preferred embodiment also via hinges.

Film hinges are provided as a particularly preferred and particularly simple embodiment for the hinges.

Preferably, the stent consists of a biocompatible material which in a particularly preferred embodiment is a nickel-titanium alloy or special steel.

These and other objects, features, aspects and advantages of the present invention will become apparent to those skilled in the art from the following detailed description, which, taken in conjunction with the annexed drawings, discloses a preferred embodiment of the present invention.

BRIEF DESCRIPTION OF THE DRAWINGS

Referring now to the attached drawings which form a part of this original disclosure.

DETAILED DESCRIPTION OF THE PREFERRED EMBODIMENTS

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

Figure 1:
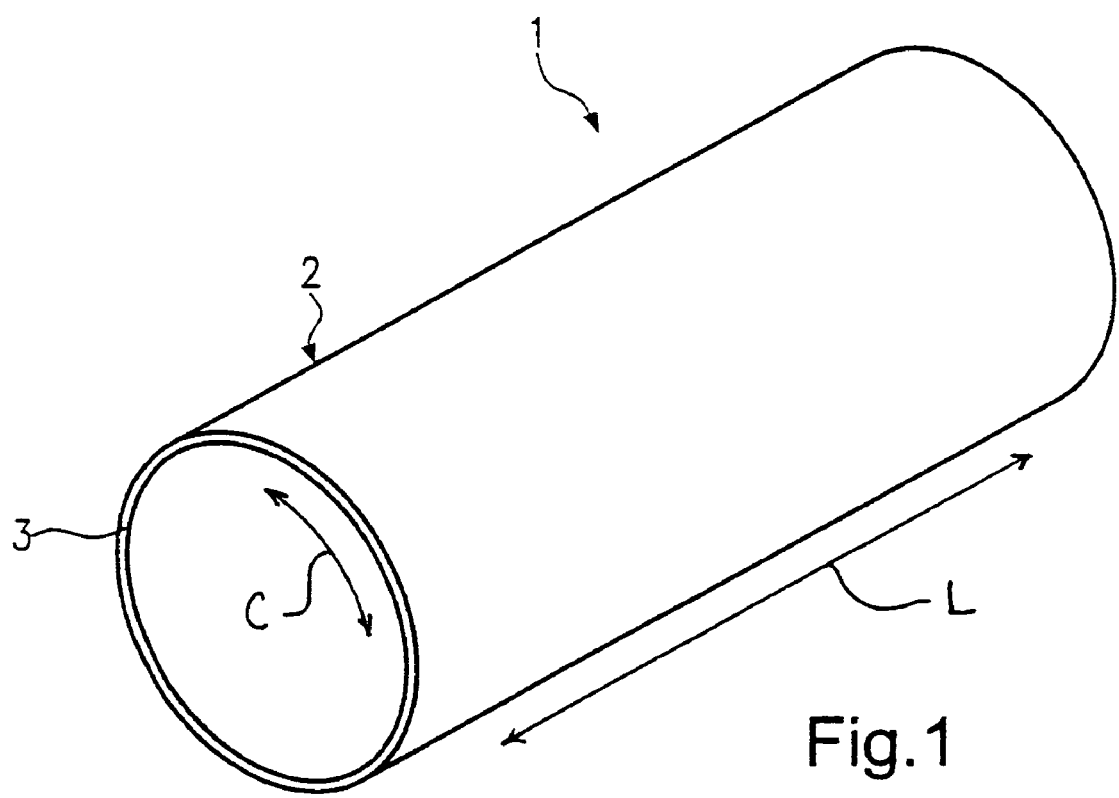
FIG. 1 is a diagrammatically very simplified schematic illustration of the basic shape of the stent according to the present invention.

Referring initially to FIG. 1, a stent 1 is diagrammatically illustrated in a very simplified schematic illustration to show the overall general shape of the stent in accordance with a first embodiment of the present invention. FIG. 1 is a front perspective view of the stent 1. The stent 1 basically comprises a flexible tubular body 2 with a tubular wall 3 with a longitudinal direction L and a circumferential direction C. The stent 1 according to the present invention can be designed as a balloon-expandable or self-expandable stent.

Figure 2:
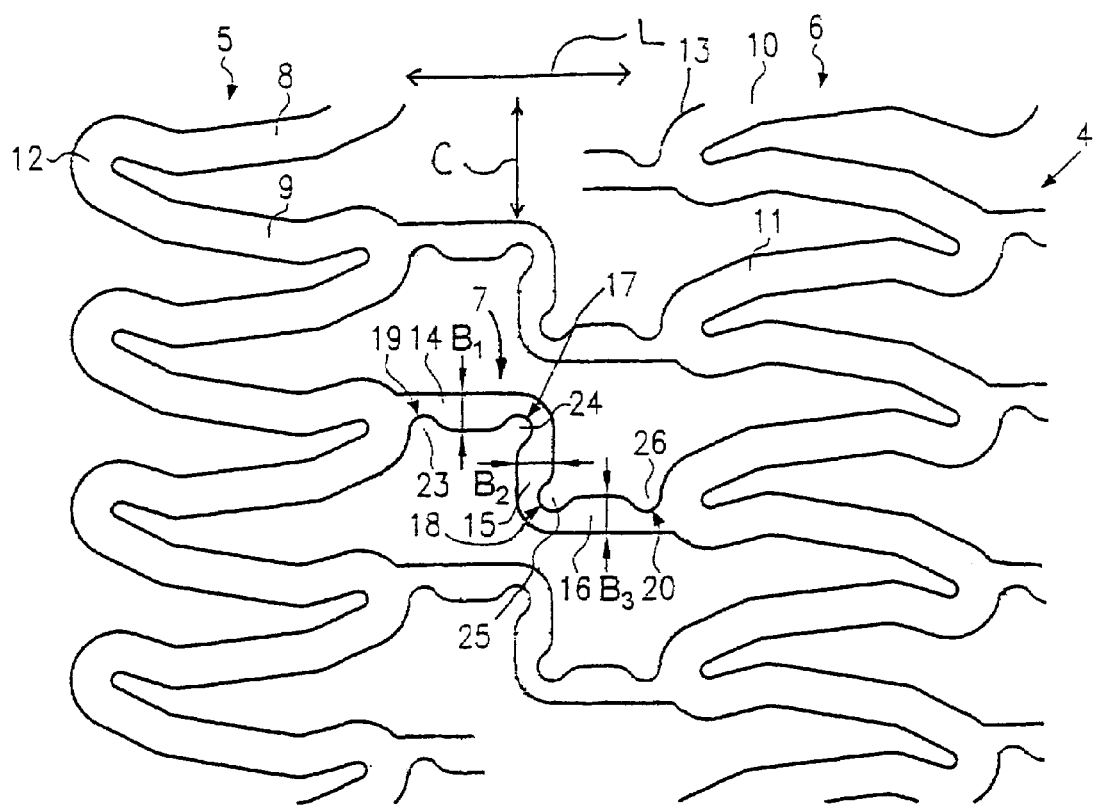
FIG. 2 is an enlarged, partial elevational view of a part of the web structure of the wall of the stent in the non-expanded state according to the present invention.

FIG. 2 shows the basic construction of the wall 3 of the body 2 of the stent 1 according to the present invention. The wall 3 of the body 2 of the stent 1 has a stent web structure 4 which can be transformed from a non-expanded state (compressed) into an expanded state. To this end the stent web structure 4 comprises a plurality of neighboring web patterns, of which only portions of web patterns 5 and 6 are illustrated in FIG. 2 by way of example. The web patterns 5 and 6 are continuous circumferentially extending rings that are axially interconnected by at least one connection element 7, preferably by a plurality of the connection elements 7 as shown. While only two web patterns 5 and 6 are shown, it will be apparent to those skilled in the art from this disclosure that there exists a plurality of web patterns 5 and 6 arranged in an alternating manner with at least one connection element 7 (preferably several connection elements 7) connecting adjacent pairs of the web patterns 5 and 6. In FIG. 2, the web pattern 5 is an end web pattern with the connection elements 7 coupled to only one of its axial sides, while the web pattern 6 is an inner web pattern with the connection elements 7 coupled to both of its axial sides. The right axial side of the web pattern 6 is coupled to a circumferential web pattern (not shown) that is identical to the web pattern 5, except the left axial side of this web pattern (not shown) is interconnected to the web pattern 6 by the connection elements 7.

As seen in FIG. 2, the web pattern 5 is formed of a plurality of first webs 8 and a plurality of second webs 9 that are arranged in an alternating manner. Each end the first webs 8 is connected to a corresponding end of one of the second webs 9 by a bend or curved section 12. Likewise, the web pattern 6 is formed of a plurality of first webs 10 and a plurality of second webs 11 that are arranged in an alternating manner. Each end the first webs 10 is connected to a corresponding end of one of the second webs 11 by a bend or curved section 13. Preferably, the web patterns of the wall 3 of the body 2 of the stent 1 alternate with the web patterns 5 and 6 such that every other web pattern look like the web pattern 5 with the web pattern 6 located therebetween and coupled together by the connection elements 7 as shown in FIG. 2.

The connection element 7 comprises three connection webs, i.e., a first outer connection web 14, a central connection web 15 and a second outer connection web 16 that are arranged at an angle relative to one another and interconnected via a pair of inner hinges 17 and 18. In particular, the connection elements 14 and 15 are interconnected via the hinge 17, and the connection webs 15 and 16 are interconnected the hinge 18. The outer connection web 14 is further connected via an outer hinge 19 to one of the bends 12, and the second outer connection web 16 via an outer hinge 20 to one of the bends 13, in accordance with the web patterns 5 and 6, respectively.

In the particularly preferred embodiment in FIG. 2, the connection webs 14, 15 and 16 are arranged at right angles relative to one another. The hinges 17, 18, 19 and 20 are designed as film hinges which are formed by providing approximately semicircular openings 24, 25, 23 and 26, respectively, in the respective connection webs 14, 15 and 16.

Figure 5:
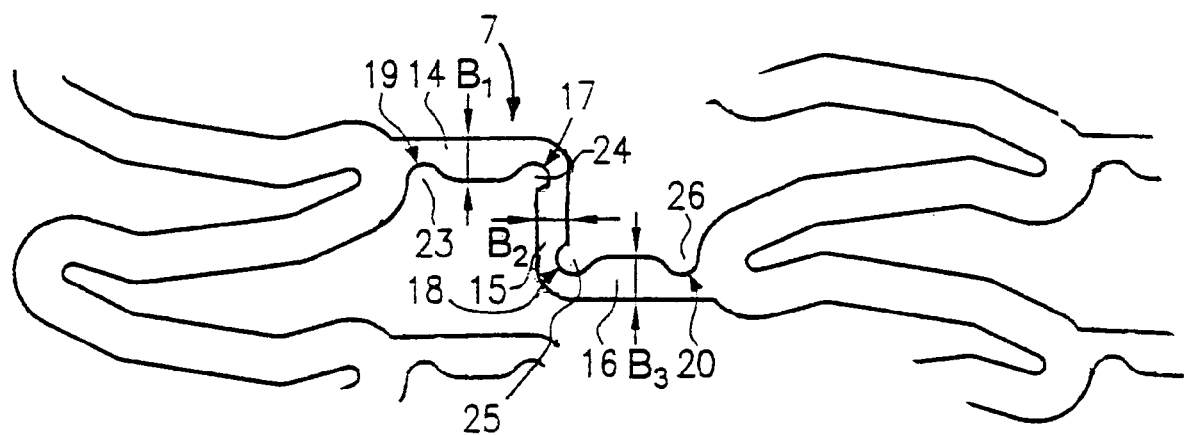
FIG. 5 is an enlarged, partial elevational view of a part of a modified connection element that can be used in place of the connection elements of the stent in FIG. 2 according to the present invention.

Preferably, the central connection web 15 has a length that is smaller than the lengths of the connection webs 14 and 16 as seen in FIG. 2. However, as seen in the alternate embodiment of FIG. 5, it is possible to make, the lengths of the webs 14, 15 and 16 all equal.

Furthermore, in the particularly preferred embodiment shown in FIG. 2, the width B1 is equal to the width B2 and the width, in turn, is equal to width B3 of the connection webs 14, 15 and 16, respectively. However, as seen in the alternate embodiment of FIG. 5, it is possible to make the width B2 of the connection web 15 smaller than the width B1 and the width B3 for increasing flexibility of the connection element 7.

Figure 3:
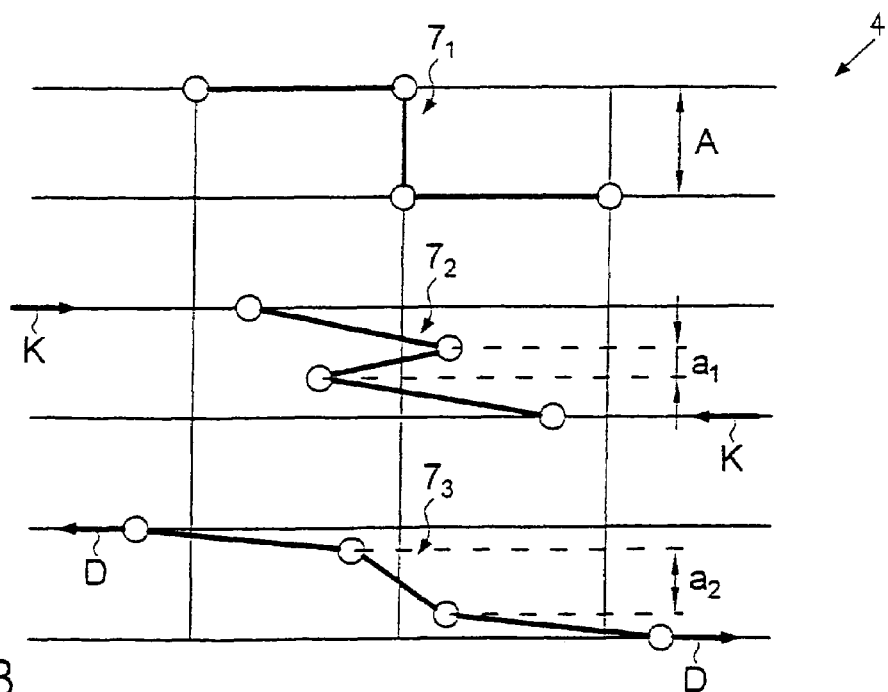
FIG. 3 is a schematic illustration of the connection elements according to the invention for explaining the function of the connection elements.

FIG. 3 illustrates the mode of operation of the connection element 7 according to the invention within the stent web structure 4. The arrangement $7_1$ shows the configuration of the connection element 7 according to FIG. 2 in a schematically simplified view. This results in a distance A of the length of the central connection web 15.

The state $7_2$ of the connection element 7 illustrates the positions of the webs 14, 15 and 16 in their compressed or unexpanded states, which are symbolized by the two arrows K. This yields a distance $a_1$ between the hinges 17 and 18 that is smaller than the distance A.

The state $7_3$, which corresponds to an expanded state, also yields a distance $a_2$ that is also smaller than the distance A.

This means that the connection element 7 is shortened both in the compressed (unexpanded) and the expanded state so that the connection elements 7 cannot protrude from the wall plane of the web structure, whereby in particular in the implanted state the surrounding tissue of the respective volume cannot be injured. Furthermore, this has the advantage that the connection elements 7 in curved vessels yield a uniform wall cover through the web patterns 5 and 6 as well as flexibility of the whole stent construction.

Figure 4A:
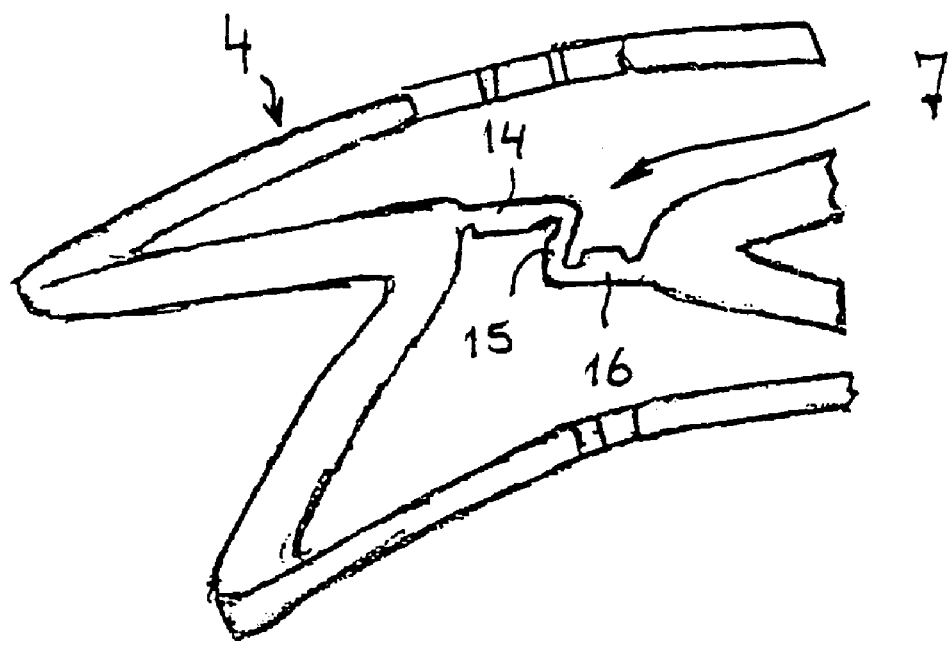
FIG. 4A is a partial diagrammatically illustration, corresponding to FIG. 2, of the arrangement of the stent according to the present invention in a non-expanded state after being inserted into a curved vessel.
Figure 4B:
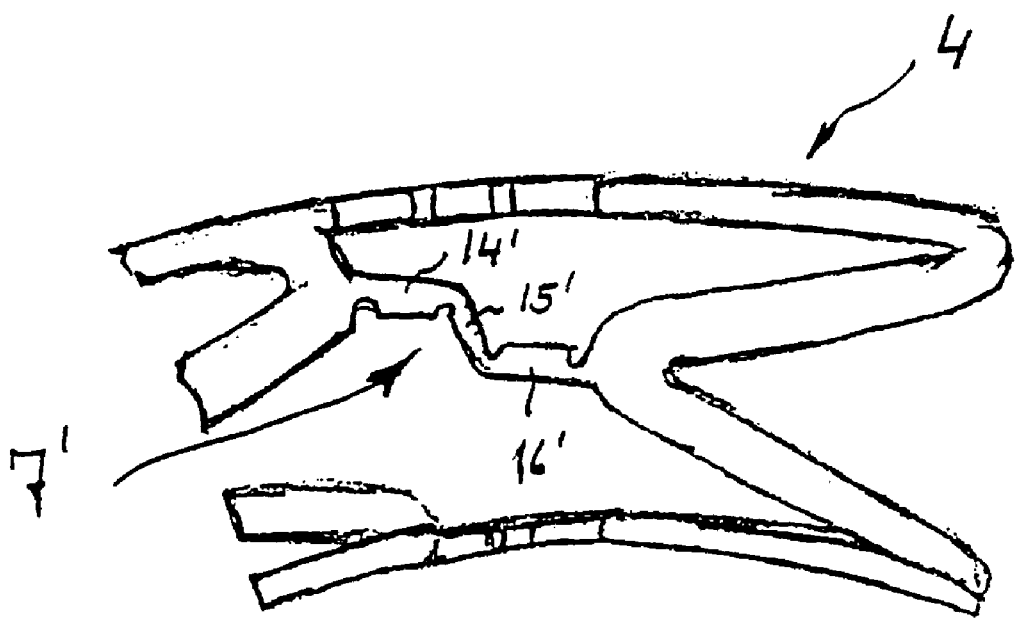
FIG. 4B is an illustration corresponding to FIG. 2 of the arrangement of the stent according to the present invention in an expanded state within a curved vessel.

Reference is here made to FIGS. 4A and 4B, each showing a section of the stent web structure 4 arranged in a curved vessel. FIG. 4A shows the compressed (unexpanded) state of the connection element 7 with its connection webs 14 to 16, whereas FIG. 4B shows and illustrates the stretched (expanded) state of a corresponding connection element 7 with its connection webs 14 to 16.

The terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

This application claims priority to European Patent Application No. 01122285.8. The entire disclosure of European Patent Application No. 01122285.8 is hereby incorporated herein by reference.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents. Thus, the scope of the invention is not limited to the disclosed embodiments.

What is claimed is:

1. A stent comprising:
   a web structure defining an essentially tubular body having a tubular wall with a longitudinal axis and a circumferential diameter, the web structure being expandable from a contracted configuration to an expanded configuration;

a plurality of longitudinally adjacent circumferential web patterns defining the web structure;

each web pattern being defined by a plurality of sequentially adjoined webs, the plurality of sequentially adjoined webs being disposed circumferentially around a longitudinal axis of the essentially tubular body; and at least one connection element extending between and connecting adjacent pairs of the web patterns configured to shorten and/or lengthen along the longitudinal axis within a curved plane defined by the tubular wall in the contracted configuration and/or the expanded configuration, the at least one connection element being formed by three connection webs, at least two being substantially non-parallel relative to one another and at least two being substantially parallel to one another, the three connection webs being disposed at an angle relative to one another, a rounded notch reducing a dimension of the connection element being formed at the junction of adjacent connection webs and at least one rounded notch disposed between a proximal end and distal end of the connection element.

2. The stent of claim 1, wherein each of the webs has a crown shape comprising a central member having a bent shape and first and a second ends, wherein the central member is disposed essentially parallel to the longitudinal axis in the contracted configuration, wherein a first end member is connected to the first end of a central member at a first obtuse angle and a second end member is connected to the second end of the central member at a second obtuse angle, and wherein adjacent pairs of webs are sequentially adjoined at central members so as to form the circumferential ring having a zigzag configuration.

3. The stent of claim 2, wherein the crown shapes in one web pattern are disposed at approximately 180 degree in relation to the crown shapes in a neighboring web pattern.

4. The stent of claim 1, wherein the three connection webs have equal widths.

5. The stent of claim 1, wherein the three connection webs have essentially the same lengths.

6. The stent of claim 1, the three connection webs of the connection element including first and second terminal connection webs and an intermediate connection web, the intermediate connection web being disposed at approximately 90 degrees relative to the first and second terminal connection webs, and the first and second terminal connection webs being disposed substantially parallel to and extending away from one another.

7. The stent of claim 1, wherein the rounded notch has an essentially semicircular configuration.

8. The stent of claim 1, wherein an area between each rounded notch and adjacent webs has a rounded shape.

9. The stent of claim 1, wherein the hinge is constructed as a film hinge.

10. The stent of claim 1, wherein the connection element is coupled to the adjacent web patterns at a first rounded notch between the connection element and one of the adjacent web patterns and at a second round notch between the connection element and the other one of the adjacent web patterns.

11. The stent of claim 1, wherein pairs of the webs are sequentially adjoined at central members, and wherein each central member in one web pattern is coupled to another central member in a neighboring web pattern by a connection element.

12. The stent of claim 1, wherein pairs of the webs are sequentially adjoined at central members, and wherein not each central member in one web pattern is coupled to another central member in a neighboring web pattern by a connection element.

13. The stent of claim 1, wherein the web structure is constructed from stainless steel or a nickel-titanium alloy.

14. The stent of claim 1, the plurality of sequentially adjoined webs including a plurality of first end members and a plurality of second end members arranged in an alternating manner with the plurality of first end members being coupled to the plurality of second end members by a plurality central members so as to form a circumferential ring around the essentially tubular body.

* * * * *

UNITED STATES PATENT AND TRADEMARK OFFICE
CERTIFICATE OF CORRECTION

PATENT NO. : 7,611,531 B2  Page 1 of 1
APPLICATION NO. : 11/435260
DATED : November 3, 2009
INVENTOR(S) : Calisse It is certified that error appears in the above-identified patent and that said Letters Patent is hereby corrected as shown below:

Column 3
Lines 33 and 38, change "end" to --end of--
Line 66, change "make," to --make--

Column 4
Lines 34 and 36, change "7" to --7'--
Line 37, change "14 to 16" to --14' to 16'--

Signed and Sealed this

Second Day of February, 2010

David J. Kappos
*Director of the United States Patent and Trademark Office*